United States Patent

[19] Haermeling

[11] Patent Number: 5,916,430
[45] Date of Patent: Jun. 29, 1999

[54] PREPARATION OF EPOXIDES

[75] Inventor: Dieter Haermeling, Frankenthal, Germany

[73] Assignee: BASF Aktiengesellschaft, Ludwigshafen, Germany

[21] Appl. No.: 08/117,378

[22] Filed: Sep. 7, 1993

Related U.S. Application Data

[63] Continuation of application No. 07/790,623, Nov. 12, 1991, abandoned.

[30] Foreign Application Priority Data

Nov. 16, 1990 [DE] Germany .............................. 40 36 511

[51] Int. Cl.[6] .............................. C25B 3/02; C07D 301/03
[52] U.S. Cl. .......................... 205/428; 205/455; 549/524
[58] Field of Search ............................ 549/524; 205/428, 205/427, 455

[56] References Cited

U.S. PATENT DOCUMENTS

| | | | |
|---|---|---|---|
| 3,394,059 | 7/1968 | Young | 204/78 |
| 3,427,235 | 2/1969 | Le Duc | 204/78 |
| 4,490,222 | 12/1984 | Davies et al. | 204/78 |
| 5,086,189 | 2/1992 | Lecloux et al. | 549/531 |

FOREIGN PATENT DOCUMENTS 50474  4/1980  Japan .

OTHER PUBLICATIONS

*Chemical Abstracts*, vol. 93, No. 6, entry 122677, (1980) no date available.
Celdran et al, *Electrochimica Acta* vol. 26, No. 6, 763–770 (Jun. 1981).
J.Chem. Soc. 1393–1395.
Houben–Weyl, vol. 5/4, 4th Ed. pp. 55 to 58 and 133–141.
Houben–Weyl, vol. 5/3, 4th Ed. pp. 775 et seq.
Tetrahedron Lett., vol. 27, 4987–4990 (1986).
Chem. Lett. 645–646 (1988).
Helv. Chim. Acta 54, 1822–1845 (1971).

*Primary Examiner*—Kishor Mayekar
*Attorney, Agent, or Firm*—Keil & Weinkauf

[57] ABSTRACT

The preparation of epoxides of the general formula I

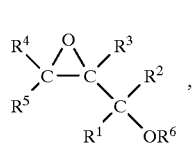

(I)

in which the substituents $R^1$, $R^2$, $R^3$, $R^4$, $R^5$ are independently hydrogen, $C_1$–$C_{20}$-alkyl, $C_3$–$C_{12}$-cycloalkyl, $C_4$–$C_{20}$-cycloalkylalkyl, $C_1$–$C_{20}$-hydroxyalkyl, a heterocyclic ring, or an aryl or $C_7$–$C_{20}$-arylalkyl group optionally substituted by $C_1$–$C_8$-alkyl, $C_1$–$C_8$-alkoxy, halogen, $C_1$–$C_4$-haloalkyl, $C_1$–$C_4$-haloalkoxy, phenyl, phenoxy, halophenyl, halophenoxy, carboxy, $C_2$–$C_8$-alkoxycarbonyl, or cyano, or $R^1$ and $R^2$ or $R^1$ and $R^3$ or $R^1$ and $R^4$ or $R^3$ and $R^4$ or $R^4$ and $R^5$ together form a $(CH_2)_n$ group in which n is an integer from 1 to 10 and which may be optionally substituted by $C_1$–$C_8$-alkyl, $C_1$–$C_8$-alkoxy, and/or halogen, and $R^6$ is hydrogen, $C_1$–$C_8$-alkyl, or benzyl, is carried out by a procedure in which an allyl alcohol of the general formula II

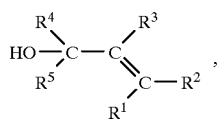

(II)

in which $R^1$, $R^2$, $R^3$, $R^4$, $R^5$ have the meanings stated above, is either
  a) electrochemically oxidized in the presence of an auxiliary electrolyte or
  b) oxidized with a halogen at a pH ranging from 7.5 to 14, in both cases in the presence of an alkanol of the general formula III

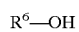

$R^6$—OH    (III), in which $R^6$ has the meaning stated above.

7 Claims, No Drawings

PREPARATION OF EPOXIDES

This application is a continuation of application Ser. No. 07/790,623, filed on Nov. 12, 1991, now abandoned.

BACKGROUND OF THE INVENTION

The present invention relates to a process for the preparation of epoxides by electrochemical oxidation of allyl alcohols in the presence of alkanols and an auxiliary electrolyte or by the reaction of allyl alcohols with halogen in the presence of alkanols in an alkaline medium, and to novel epoxides.

*J. Chem. Soc.* 1393–1395 (1948) discloses the reaction of chlorine with allyl alcohol in an acid medium to yield 2,3-dichloropropanol. According to *Houben-Weyl*, Vol. 5/4, 4th Edition, pp. 55 to 58 and 133 to 141, bromohydrins can be produced under comparable conditions by reacting allyl alcohols with bromine or bromine having the degree of oxidation (+1).

According to *Houben-Weyl* 5/3, 4th Edition, pp. 775 et seq and *Houben-Weyl* 5/4, 4th Edition, pp. 141–146, the reaction of olefins with chlorine or chlorine having the degree of oxidation (+1) or with bromine or bromine having the degree of oxidation (+1) in the presence of alcohol yields, on the other hand, halohydrin ethers.

The synthesis of 3-substituted 3-hydroxy-1,2-epoxides from 3-substituted alk-2-en-1-ols is only possible, according to *Tetrahedron Lett.* 27, 4987–4990 (1986) and *Chem. Lett.* 645–646 (1988), via a separate stage involving the isomerization of the initially synthesized 3-substituted 1-hydroxy-2,3-epoxides, or, as described in *Helv. Chim. Acta* 54, 1822–1845 (1971), the isomerization is carried out at the allyl alcohol level.

The direct synthesis of 3-hydroxy-1,2-epoxides or 3-alkoxy-1,2-epoxides from 1-hydroxyalk-2-enes where the oxygen atom in the educt becomes the epoxide oxygen atom of the product has not yet been disclosed.

It is thus an object of the invention to provide such a method of direct synthesis.

BRIEF SUMMARY OF THE INVENTION

Accordingly, we have found a novel process for the preparation of epoxides of the general formula I

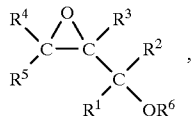
(I)

in which the substituents $R^1$, $R^2$, $R^3$, $R^4$, $R^5$ are independently hydrogen, $C_1$–$C_{20}$-alkyl, $C_3$–$C_{12}$-cycloalkyl, $C_4$–$C_{20}$-cycloalkylalkyl, $C_1$–$C_{20}$-hydroxyalkyl, a heterocyclic ring, or an aryl or $C_7$–$C_{20}$-arylalkyl group optionally substituted by $C_1$–$C_8$-alkyl, $C_1$–$C_8$-alkoxy, halogen, $C_1$–$C_4$-haloalkyl, $C_1$–$C_4$-haloalkoxy, phenyl, phenoxy, halophenyl, halophenoxy, carboxy, $C_2$–$C_8$-alkoxycarbonyl, or cyano, or $R^1$ and $R^2$ or $R^1$ and $R^3$ or $R^1$ and $R^4$ or $R^3$ and $R^4$ or $R^4$ and $R^5$ together form a $(CH_2)_n$ group in which n is an integer from 1 to 10 and which may be optionally substituted by $C_1$–$C_8$-alkyl, $C_1$–$C_8$-alkoxy, and/or halogen, and $R^6$ is hydrogen, $C_1$–$C_8$-alkyl, or benzyl, wherein an allyl alcohol of the general formula II

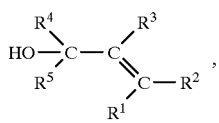
(II)

in which $R^1$, $R^2$, $R^3$, $R^4$, $R^5$ have the meanings stated above, is either a) electrochemically oxidized in the presence of an auxiliary electrolyte or b) oxidized with a halogen at a pH ranging from 7.5 to 14, in both cases in the presence of a compound of the formula III

(III), in which $R^6$ has the meaning stated above.

We have also found novel compounds of the general formula IV

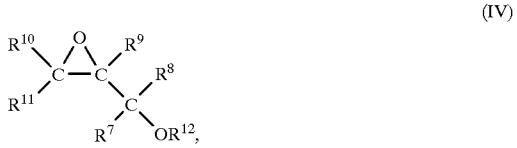
(IV)

in which the substituents have the following meanings:

$R^7$, $R^8$, $R^9$, $R^{10}$, $R^{11}$ are independently hydrogen, $C_1$–$C_{20}$-alkyl, $C_3$–$C_{12}$-cycloalkyl, $C_4$–$C_{20}$-cycloalkylalkyl, $C_1$–$C_{20}$-hydroxyalkyl, a heterocyclic ring, or an aryl or $C_7$–$C_{20}$-arylalkyl group optionally substituted by $C_1$–$C_8$-alkyl, $C_1$–$C_8$-alkoxy, halogen, $C_1$–$C_4$-haloalkyl, $C_1$–$C_4$-haloalkoxy, phenyl, phenoxy, halophenyl, halophenoxy, carboxy, $C_2$–$C_8$-alkoxycarbonyl, or cyano, or $R^7$ and $R^8$ or $R^7$ and $R^9$ or $R^7$ and $R^{10}$ or $R^9$ and $R^{10}$ or $R^{10}$ and $R^{11}$ together form a $(CH_2)_n$ group in which n is an integer from 1 to 10 and which may be optionally substituted by $C_1$–$C_8$-alkyl, $C_1$–$C_8$-alkoxy, and/or halogen, and $R^{12}$ is hydrogen, $C_1$–$C_8$-alkyl, or benzyl, provided that $R^{10}$ is not hydrogen, methyl, ethyl, propyl, or cyclohexyl when $R^7$, $R^8$, $R^9$, or $R^{11}$ is hydrogen, that $R^7$ is not methyl when $R^8$ is methyl or phenyl and $R^9$, $R^{10}$, or $R^{11}$ is hydrogen, that $R^7$ is not methyl when $R^8$, $R^9$, $R^{10}$, or $R^{11}$ is hydrogen and $R^{12}$ is ethyl, that $R^7$ is not phenyl or hexyl when $R^8$, $R^9$, $R^{10}$, or $R^{11}$ is hydrogen, that $R^9$ is not methyl when $R^7$, $R^8$, $R^{10}$, or $R^{11}$ is hydrogen, that $R^{10}$ and $R^{11}$ are not methyl when $R^7$, $R^8$, or $R^9$ is hydrogen, and that $R^7$ and $R^{10}$ do not together form an unsubstituted cycloalkyl when $R^8$, $R^9$, or $R^{11}$ is hydrogen.

Suitable starting materials for the preparation of the epoxides of the invention are basically all allyl alcohols of the general formula II which carry substituents which are inert under the conditions of electrolysis.

DETAILED DESCRIPTION OF THE INVENTION

For our novel process, the following are suitable values for the substituents $R^1$ to $R^6$, independently of each other, and for the index n in the formulae I to III:

$R^1$, $R^2$, $R^3$, $R^4$, $R^5$—hydrogen, unbranched or branched $C_1$–$C_{20}$-alkyl, preferably unbranched or branched $C^1$–$C^{12}$-alkyl, such as methyl, ethyl, n-propyl, isopropyl, n-butyl, isobutyl, s-butyl, t-butyl, n-pentyl, isopentyl, s-pentyl, t-pentyl, neopentyl, 1,2-dimethylpropyl, n-hexyl, isohexyl, r-hexyl, n-heptyl, isoheptyl, n-octyl, isooctyl, n-nonyl, isononyl, n-decyl, isodecyl, n-undecyl, iso-undecyl, n-dodecyl, and iso-dodecyl, $C_3$–$C_{12}$-cycloalkyl, preferably $C_3$–$C_8$-cycloalkyl, such as cyclopropyl, cyclobutyl, cyclopentyl, cyclohexyl, cycloheptyl, and cyclooctyl, $C_4$–$C_{20}$-cycloalkylalkyl, preferably $C_4$–$C_8$-cycloalkylalkyl, such as cyclopentylalkyl, 2-cyclopentylethyl, 1-cyclopentylethyl, cycloalkylmethyl, 1-cyclohexylethyl, and 2-cyclohexylethyl, unbranched or branched $C_1$–$C_{20}$-hydroxyalkyl, preferably unbranched or branched $C_1$–$C_8$-hydroxyalkyl, such as hydroxymethyl, 1-hydroxyethyl, 2-hydroxyethyl, 1-hydroxypropyl, 2-hydroxypropyl, and 3-hydroxypropyl, a heterocyclic ring such as a 3-membered to 12-membered heterocyclic ring, preferably a 3-membered to 8-membered heterocyclic ring, such as oxiranyl, tetrahydrofuran-2-yl, tetrahydrofuran-3-yl, tetrahydropyran-2-yl, tetrahydropyran-3-yl, tetrahydropyran-4-yl, 1,3-dioxolan-2-yl, 1,3-dioxolan-4-yl, dioxan-2-yl, pyrrolidin-2-yl, N-methylpyrrolidin-2-yl, 1yl-methylpyrrolidin-3-yl, pyrrolidin-3-yl, piperidin-2-yl, piperidin-3-yl, piperidin-4-yl, morpholin-2-yl, and morpholin-3-yl, aryl, such as phenyl, 1-naphthyl, and 2-naphthyl, preferably phenyl, aryl mono- to tri-substituted by $C_1$–$C_8$-alkyl, preferably phenyl mono- to tri-substituted by $C_1$–$C_4$-alkyl, such as 2-methylphenyl, 4-methylphenyl, 2-ethylphenyl, 4-ethylphenyl, 3-methylphenyl, 2,4-dimethylphenyl, 3,4-dimethylphenyl, and 3,4,5-trimethylphenyl, aryl mono- to tri-substituted by $C_1$–$C_8$-alkoxy, preferably phenyl mono- to tri-substituted by $C_1$–$C_4$-alkoxy, such as 2-methoxyphenyl, 2-ethoxyphenyl, 3-methoxyphenyl, 4-methoxyphenyl, 3-ethoxyphenyl, 4-ethoxyphenyl, 3,4-dimethoxyphenyl, and 3,4,5-trimethoxyphenyl, aryl mono- to tri-substituted by $C_1$–$C_4$-haloalkyl, preferably phenyl mono- to tri-substituted by $C_1$–$C_2$-fluoroalkyl and $C_1$–$C_2$-chloroalkyl, more preferably phenyl mono- to tri-substituted by trifluoromethyl and trichloroethyl, such as 4-trifluoromethylphenyl and 4-trichloromethylphenyl, aryl mono- to tri-substituted by $C_1$–$C_4$-haloalkoxy, preferably phenyl mono- to tri-substituted by $C_1$–$C_2$-fluoroalkoxy and $C_1$–$C_2$-chloroalkoxy, more preferably phenyl mono- to tri-substituted by trifluoromethoxy and trichloroethoxy, such as trifluoromethoxyphenyl, aryl mono- to tri-substituted by halogen, preferably phenyl mono- to tri-substituted by fluorine, chlorine, and bromine, such as 4-chlorophenyl, 3,4-dichlorophenyl, 4-bromophenyl, 4-fluorophenyl, and 4-fluoro-3-chlorophenyl, aryl mono- to tri-substituted by halophenyl, preferably phenyl mono- to tri-substituted by fluorophenyl and/or chlorophenyl, such as (4-chlorophenyl)phenyl, aryl mono- to tri-substituted by halophenoxy, preferably phenyl mono- to tri-substituted by fluorophenoxy and/or chlorophenoxy, such as (4-fluorophenoxy)phenyl, aryl mono- to tri-substituted by carboxy, preferably phenyl mono- to tri-substituted by carboxy, such as 2-carboxyphenyl, 3-carboxyphenyl, and 4-carboxyphenyl, aryl mono- to tri-substituted by $C_2$–$C_8$-alkoxycarbonyl, preferably phenyl mono- to tri-substituted by $C_2$–$C_4$-alkoxycarbonyl, such as 4-methoxycarbonylphenyl, 4-ethoxycarbonylphenyl, 2-methoxycarbonylphenyl, 2-ethoxycarbonylphenyl, and 3-methoxycarbonylphenyl, aryl mono- to tri-substituted by cyano, preferably phenyl mono- to tri-substituted by cyano, such as 2-cyanophenyl, 3-cyanophenyl, and 4-cyanophenyl, $C_7$–$C_{20}$-arylalkyl, preferably $C_7$–$C_{12}$-arylalkyl, such as benzyl, phenylethyl, phenylpropyl, and phenylisopropyl, $C_7$–$C_{20}$-arylalkyl mono- to tri-substituted in the aryl moiety by halogen, preferably $C_7$–$C_{10}$-phenylalkyl mono- to tri-substituted in the phenyl moiety by fluorine or chlorine, such as 4-fluorobenzyl, 4-chlorobenzyl, 2,4-dichlorobenzyl, and 3,4-dichlorobenzyl, $C_7$–$C_{20}$-arylalkyl mono- to tri-substituted in the aryl moiety by $C_1$–$C_8$-alkyl, preferably $C_7$–$C_{10}$-phenylalkyl mono- to tri-substituted in the phenyl moiety by $C_1$–$C_4$-alkyl, more preferably $C_7$–$C_{10}$-phenylalkyl mono- to tri-substituted in the phenyl moiety by $C_1$–$C_2$-alkyl, such as 4-methylphenyl, 4-ethylbenzyl, and 4-methylphenethyl, $C_7$–$C_{20}$-arylalkyl mono- to tri-substituted in the aryl moiety by $C_1$–$C_8$-alkoxy, preferably $C_7$–$C_{10}$-phenylalkyl mono- to tri-substituted in the phenyl moiety by $C_1$–$C_4$-alkoxy, more preferably $C_7$–$C_{10}$-phenylalkyl mono- to tri-substituted in the phenyl moiety by $C_1$–$C_2$-alkoxy, such as 4-methoxybenzyl, 4-ethoxybenzyl, and 4-methoxyphenethyl, $C_7$–$C_{20}$-arylalkyl mono- to tri-substituted in the aryl moiety by $C_1$–$C_4$-haloalkyl, preferably $C_7$–$C_{10}$-phenylalkyl mono- to tri-substituted in the phenyl moiety by $C_1$–$C_2$fluoroalkyl and $C_1$–$C_2$-chloroalkyl, more preferably $C_7$–$C_{10}$-phenylalkyl mono- to tri-substituted in the phenyl $C_{10}$-phenylalkyl mono- to tri-substituted in the phenyl moiety by trifluoromethyl and trichloromethyl, such as 4-trifluoromethylbenzyl and 4-trichloromethylbenzyl, $C_7$–$C_{20}$-arylalkyl mono- to tri-substituted in the aryl moiety by $C_1$–$C_4$-haloalkoxy, preferably $C_7$–$C_{10}$-phenylalkyl mono- to tri-substituted in the phenyl moiety by $C_1$–$C_2$-haloalkoxy, more preferably $C_7$–$C_{10}$-phenylalkyl mono- to tri-substituted in the phenyl moiety by trifluoromethoxy and trichloromethoxy, such as 4-trifluoromethoxybenzyl and 4-trichloromethoxybenzyl, $C_7$–$C_{20}$-arylalkyl mono- to tri-substituted by halophenyl, preferably $C_7$–$C_{12}$-phenylalkyl mono- to tri-substituted by fluorophenyl and/or chlorophenyl, such as 4-chlorophenethyl and 4-fluorophenethyl, $C_7$–$C_{20}$-arylalkyl mono- to tri-substituted by halophenoxy, preferably $C_7$–$C_{12}$-phenylalkyl mono- to tri-substituted by fluorophenoxy and/or chlorophenoxy, such as 2-chlorophenoxymethyl and 4-chlorophenoxymethyl, $C_7$–$C_{20}$-arylalkyl mono- to tri-substituted by carboxy, preferably $C_7$–$C_{12}$-phenylalkyl mono- to trisubstituted by carboxy, such as 4-carboxybenzyl, 4-carboxyphenethyl, 2-carboxybenzyl, and 4-carboxyphenylethyl, $C_7$–$C_{20}$-arylalkyl mono- to tri-substituted by $C_2$–$C_8$-alkoxycarbonyl, preferably $C_7$–$C_{12}$-phenylalkyl mono- to tri-substituted by $C_2$–$C_4$-alkoxycarbonyl, such as 4-methoxycarbonylbenzyl, 2-methoxycarbonylbenzyl, 4-ethoxycarbonylbenzyl, and 2-ethoxycarbonylbenzyl, $C_7$–$C_{20}$-arylalkyl mono- to tri-substituted by cyano, preferably $C_7$–$C_{12}$-phenylalkyl mono- to tri-substituted by cyano, such as 2-cyanobenzyl, 4-cyanobenzyl, 2-cyanophenethyl, and 4-cyanophenethyl, phenyl substituted by one, two, or three phenyl groups, such as 2-(phenyl)phenyl, 3-(phenyl)phenyl, 4-(phenyl)phenyl, and 3,4-(diphenyl)phenyl, phenyl substituted by one, two, or three phenoxy groups, such as 4-phenoxyphenyl and 2-phenoxyphenyl, phenyl di- or tri-substituted by halogen and $C_1$–$C_4$-alkyl, such as 2-methyl-4-chlorophenyl and 3-methyl-4-fluorophenyl, phenyl di- or tri-substituted by halogen and $C_1$–$C_4$-alkoxy, such as 3-chloro-4-methoxyphenyl, phenyl di- or tri-substituted by halogen and $C_1$–$C_4$-haloalkyl, such as 2-chloro-4-trifluoromethylphenyl, phenyl di- or tri-substituted by halogen and phenoxy, such as 3-chloro-4-phenoxyphenyl, phenyl di- or tri-substituted by $C_1$–$C_4$-alkyl and $C_1$–$C_4$-alkoxy, such as 2-methyl-4-methoxyphenyl, phenyl di- or tri-substituted by $C_1$–$C_4$-alkyl and $C_1$–$C_4$-haloalkyl, such as 3-methyl-4-trichloromethylphenyl, phenyl di- or tri-substituted by $C_1$–$C_4$-alkyl and phenoxy, such as 2-methyl-4-phenoxyphenyl, phenyl di- or tri-substituted by $C_1$–$C_4$-alkoxy and $C_1$–$C_4$-haloalkyl, such as 3-trifluoromethyl-4-methoxyphenyl, phenyl di- or tri-substituted by $C_1$–$C_4$-alkoxy and phenoxy, such as 3-methoxy-4-phenoxyphenyl, phenyl di- or tri-substituted by $C_1$–$C_4$-haloalkyl and phenoxy, such as 3-trifluoromethyl-4-phenoxyphenyl, phenyl trisubstituted by halogen, $C_1$–$C_4$-alkyl, and $C_1$–$C_4$-alkoxy, such as 2-chloro-3-t-butyl-4-methoxyphenyl, phenyl trisubstituted by halogen, $C_1$–$C_4$-alkyl, and $C_1$–$C_4$-haloalkyl, such as 2-methyl-3-chloro-4-trifluoromethylphenyl, phenyl trisubstituted by halogen, $C_1$–$C_4$-alkyl, and phenoxy, such as 4-chloro-2-ethyl-3-phenoxyphenyl, phenyl trisubstituted by halogen, $C_1$–$C_4$-alkoxy, and $C_1$–$C_4$-haloalkyl, such as 3-chloro-4-methoxy-3-trifluoromethyl, phenyl trisubstituted by halogen, $C_1$–$C_4$-alkoxy, and phenoxy, such as 2-fluoro-4-ethoxy-3-phenoxyphenyl, phenyl trisubstituted by halogen, $C_1$–$C_4$-haloalkyl, and phenoxy, such as 4-fluoro-3-trifluoromethyl-2-phenoxyphenyl, phenyl trisubstituted by $C_1$–$C_4$-alkyl, $C_1$–$C_4$-alkoxy, and $C_1$–$C_4$-haloalkyl, such as 4-methyl-3-methoxy-2-trichloromethylphenyl, phenyl trisubstituted by $C_1$–$C_4$-alkyl, $C_1$–$C_4$-alkoxy, and phenoxy, such as 4-methyl-3-ethoxy-2-phenoxyphenyl, phenyl trisubstituted by $C_1$–$C_4$-alkyl, $C_1$–$C_4$-haloalkyl, and phenoxy, such as 2-methyl-4-trifluoromethyl-3-phenoxyphenyl, phenyl trisubstituted by $C_1$–$C_4$-alkoxy, $C_1$–$C_4$-haloalkyl, and phenoxy, such as 4-methoxy-2-trichloromethyl-3-phenoxyphenyl, or $R^1$ and $R^2$ or $R^1$ and $R^3$ or $R^1$ and $R^4$ or $R^3$ and $R^4$ or $R^4$ and $R^5$ together form $(CH_2)_n$, such as $CH_2$, $(CH_2)_2$, $(CH_2)_3$, $(CH_2)_4$, $(CH_2)_5$, and $(CH_2)_6$, preferably $(CH_2)_3$, $(CH_2)_4$, $(CH_2)_5$, and $(CH_2)_6$, more preferably $(CH_2)_3$ and $(CH_2)_4$, n an integer from 1 to 6, preferably from 3 to 6, more preferably 3 or 4, $R^6$—hydrogen, $C_1$–$C_8$-alkyl, preferably $C_1$–$C_4$-alkyl, such as methyl, ethyl, n-propyl, and n-butyl, benzyl.

By "mono- to tri-substituted" we mean monosubstituted, disubstituted or trisubstituted.

The process variants a) and b) can be carried out as follows:

Both the electrochemical oxidation and the reaction with halogen can be carried out in an alkaline medium at a temperature of from –20° to 150° C. and preferably from 0° to 100° C. under a pressure of from 0.01 to 50 bar, preferably from 0.1 to 5 bar, more preferably atmospheric pressure (standard pressure).

a) In order to achieve adequate electrolysis-conductivity of the electrolyte, a preferably halogen-containing auxiliary electrolyte is added to the electrolysis mixture. Examples of suitable auxiliary electrolytes are elementary halogen, alkyl halides, hydrogen halide, and halides such as iodides and bromides, eg ammonium halides such as ammonium bromide, ammonium iodide, and tetrabutylammonium iodide, and particular preference is given to metal halides such as sodium bromide, sodium iodide, potassium bromide, and potassium iodide.

If the conductivity of the halogen compound alone is inadequate, it may be supplemented by other auxiliary electrolytes commonly used in electrochemistry, examples of which are tetrafluoroborates, tetraalkylammonium salts such as tetraethylammoniumbenzene sulfonate, perchlorates such as $LiClO_4$, methylates such as sodium methylate, and hydroxides such as NaOH or KOH.

The composition of the electrolyte can be varied within wide limits. It preferably contains from 1 to 49, preferably from 5 to 30% w/w of allyl alcohol II, from 50 to 98.9, preferably from 70 to 95% w/w of compound $R^7$—OH, and from 0.1 to 5, preferably from 0.5 to 3% w/w of auxiliary electrolyte (catalytic amounts).

The electrolyte may contain from 0 to 10% w/w of water.

The electrochemical oxidation is preferably carried out at a current density ranging from 0.5 to 25 A/dm$^2$ and at a temperature of from 0° to 100° C. and preferably from 100 to 50° C. The reaction can be carried out at reduced, elevated, or, preferably, standard pressure (atmospheric pressure) in a conventional electrolytic cell, preferably an undivided flow cell.

Suitable anode materials are, for example, noble metals such as platinum, or oxides such as ruthenium and chromium oxides or mixed oxides of the formula $RuO_x/TiO_x$, or preferably graphite.

Generally suitable cathode materials are iron, steel, nickel, and noble metals such as platinum, and preferably graphite.

b) The non-electrochemical epoxidation of the invention—the reaction of halogens with allyl alcohols in an alkaline medium—is not affected by concentration factors to a very large extent. For example, from 1 to 30% w/w and preferably from 3 to 25% w/w solutions of allyl alcohol of formula II in from 40 to 98% w/w and preferably from 50 to 94% w/w of solvent $R^6$—OH and from 1 to 30% w/w and preferably from 3 to 25% w/w of base can be used. The base used is preferably one of the formula $R^6O^{\ominus}X^{\oplus}$, where $X^{\oplus}$ is a metal cation, preferably an alkali metal or alkaline earth metal cation. The oxidizing agent is preferably added at such a rate that the temperature of the reaction mixture rises by not more than 30° C. The oxidizing agent may be added in an equimolar amount or in excess, ie in a molar ratio of from 1:1 to 50:1, Preferably from 1:1 to 5:1. The reaction may be carried to completion, but it is preferred to effect only partial conversion, since this usually gives better selectivity. The amount of base used is such that an alkaline medium is maintained whatever the concentration of the oxidizing agent. The manner in which the reactants are added is not critical. For example, the base and oxidizing agent may, if desired, be added concurrently to a solution consisting of from 1 to 30% w/w of a compound of formula II and from 70 to 99% w/w of a compound of the formula $R^7$—OH. Both the oxidizing agent and the base can be used in substance or dissolved in an inert solvent such as $CCl_4$ or added to the compound $R^7$—OH. An inverse procedure is likewise possible, that is to say, the oxidizing agent may be initially taken in substance or in the form of a solution, and the base and compound of formula II, either in substance or solution, may be added thereto, or the compound of formula II may be added to a mixture of oxidizing agent and base.

The above description of the procedure implies that the initial substance(s) taken may comprise only a portion of the total amount of said substance(s), the remainder being added later. The oxidation may be carried out batchwise or continuously.

The reaction with halogen at a pH of from 7.5 to 14 and preferably from 8 to 14 is suitably carried out using elementary halogen such as fluorine, chlorine, bromine, and iodine, preferably chlorine, bromine, and iodine in a base, hypohalites such as hypochlorite, hypobromite, and hypoiodite, reagents which release a halogen having a degree of oxidation of (0) or (+1), such as N-chlorosuccinimide, N-bromosuccinimide, Chloramin® T, tetraalkylammonium bromide/bromine complexes, benzenesulfonic dichloride, and phenyl iodide dichloride, in a base.

Suitable bases are metal alkyls such as butyl lithium and methyl lithium, amides such as sodium amide and lithium diisopropylamide, hydrides such as sodium hydride, and, preferably, NaOH, KOH, LiOH, or alcoholates such as sodium ethylate and sodium methylate.

Isolation of the product is carried out in known manner. The compounds of the invention are preferably worked up by distillation.

The substituents present in the compounds of the invention of the general formula IV have the following values:
$R^7$, $R^8$, $R^9$, $R^{10}$, $R^{11}$ are, independently of each other,
hydrogen,
unbranched or branched $C_1$–$C_{20}$-alkyl, preferably unbranched or branched $C_1$–$C_{12}$-alkyl, such as methyl, ethyl, n-propyl, isopropyl, n-butyl, isobutyl, s-butyl, t-butyl, n-pentyl, isopentyl, s-pentyl, t-pentyl, neopentyl, 1,2-dimethylpropyl, n-hexyl, isohexyl, s-hexyl, n-heptyl, isoheptyl, n-octyl, isooctyl, n-nonyl, isononyl, n-decyl, isodecyl, n-undecyl, iso-undecyl, n-dodecyl, and isododecyl, $C_3$–$C_{12}$-cycloalkyl, preferably $C_3$–$C_8$-cycloalkyl, such as cyclopropyl, cyclobutyl, cyclopentyl, cyclohexyl, cycloheptyl, and cyclooctyl, $C_4$–$C_{20}$-cycloalkylalkyl, preferably $C_4$–$C_8$-cycloalkylalkyl, such as cyclopentylalkyl, 2-cyclopentylethyl, 1-cyclopentylethyl, cycloalkylmethyl, 1-cyclohexylethyl, and 2-cyclohexylethyl, unbranched or branched $C_1$–$C_{20}$-hydroxyalkyl, preferably unbranched or branched $C_1$–$C_8$-hydroxyalkyl, such as hydroxymethyl, 1-hydroxyethyl, 2-hydroxyethyl, 1-hydroxypropyl, 2-hydroxypropyl, and 3-hydroxypropyl, a heterocyclic ring such as a 3-membered to 12-membered heterocyclic ring, preferably a 3-membered to 8-membered heterocyclic ring, such as oxiranyl, tetrahydrofuran-2-yl, tetrahydrofuran-3-yl, tetrahydropyran-2-yl, tetrahydropyran-3-yl, tetrahydropyran-4-yl, 1,3-dioxolan-2-yl, 1,3-dioxolan-4-yl, dioxan-2-yl, pyrrolidin-2-yl, N-methylpyrrolidin-2-yl, N-methylpyrrolidin-3-yl, pyrrolidin-3-yl, piperidin-2-yl, piperidin-3-yl, piperidin-4-yl, morpholin-2-yl, and morpholin-3-yl, aryl, such as phenyl, 1-naphthyl, and 2-naphthyl, preferably phenyl, aryl mono- to tri-substituted by $C_1$–$C_8$-alkyl, preferably phenyl mono- to tri-substituted by $C_1$–$C_4$-alkyl, such as 2-methylphenyl, 4-methylphenyl, 2-ethylphenyl, 4-ethylphenyl, 3-methylphenyl, 2,4-dimethylphenyl, 3,4-dimethylphenyl, and 3,4,5-trimethylphenyl, aryl mono- to tri-substituted by $C_1$–$C_8$-alkoxy, preferably phenyl mono- to tri-substituted by $C_1$–$C_4$-alkoxy, such as 2-methoxyphenyl, 2-ethoxyphenyl, 3-methoxyphenyl, 4-methoxyphenyl, 3-ethoxyphenyl, 4-ethoxyphenyl, 3,4-dimethoxyphenyl, and 3,4,5-trimethoxyphenyl, aryl mono- to tri-substituted by $C_1$–$C_4$-haloalkyl, preferably phenyl mono- to tri-substituted by $C_1$–$C_2$-fluoroalkyl and $C_1$–$C_2$-chloroalkyl, more preferably phenyl mono- to tri-substituted by trifluoromethyl and trichloroethyl, such as 4-trifluoromethylphenyl and 4-trichloromethylphenyl, aryl mono- to tri-substituted by $C_1$–$C_4$-haloalkoxy, preferably phenyl mono- to tri-substituted by $C_1$–$C_2$-fluoroalkoxy and $C_1$–$C_2$-chloroalkoxy, more preferably phenyl mono- to tri-substituted by trifluoromethoxy and trichloroethoxy, such as trifluoromethoxyphenyl, aryl mono- to tri-substituted by halogen, preferably phenyl mono- to tri-substituted by fluorine, chlorine, and bromine, such as 4-chlorophenyl, 3,4-dichlorophenyl, 4-bromophenyl, 4-fluorophenyl, and 4-fluoro-3-chlorophenyl, aryl mono- to tri-substituted by halophenyl, preferably phenyl mono- to tri-substituted by fluorophenyl and/or chlorophenyl, such as (4-chlorophenyl)phenyl, aryl mono- to tri-substituted by halophenoxy, preferably phenyl mono- to tri-substituted by fluorophenoxy and/or chlorophenoxy, such as (4-fluorophenoxy)phenyl, aryl mono- to tri-substituted by carboxy, preferably phenyl mono- to tri-substituted by carboxy, such as 2-carboxyphenyl, 3-carboxyphenyl, and 4-carboxyphenyl, aryl mono- to tri-substituted by $C_2$–$C_8$-alkoxycarbonyl, preferably phenyl mono- to tri-substituted by $C_2$–$C_4$-alkoxycarbonyl, such as 4-methoxycarbonylphenyl, 4-ethoxycarbonylphenyl, 2-methoxycarbonylphenyl, 2-ethoxycarbonylphenyl, and 3-methoxycarbonylphenyl, aryl mono- to tri-substituted by cyano, preferably phenyl mono- to tri-substituted by cyano, such as 2-cyanophenyl, 3-cyanophenyl, and 4-cyanophenyl, $C_7$–$C_{20}$-arylalkyl, preferably $C_7$–$C_{12}$-arylalkyl, such as benzyl, phenylethyl, phenylpropyl, and phenylisopropyl, $C_7$–$C_{20}$-arylalkyl mono- to tri-substituted in the aryl moiety by halogen, preferably $C_7$–$C_{10}$-phenylalkyl mono- to tri-substituted in the phenyl moiety by fluorine or chlorine, such as 4-fluorobenzyl, 4-chlorobenzyl, 2,4-dichlorobenzyl, and 3,4-dichlorobenzyl, $C_7$–$C_{20}$-arylalkyl mono- to tri-substituted in the aryl moiety by $C_1$–$C_8$-alkyl, preferably $C_7$–$C_{10}$-phenylalkyl mono- to tri-substituted in the phenyl moiety by $C_1$–$C_4$-alkyl, more preferably $C_7$–$C_{10}$-phenylalkyl mono- to tri-substituted in the phenyl moiety by $C_1$–$C_2$-alkyl, such as 4-methylphenyl, 4-ethylbenzyl, and 4-methylphenethyl, $C_7$–$C_{20}$-arylalkyl mono- to tri-substituted in the aryl moiety by $C_1$–$C_8$-alkoxy, preferably $C_7$–$C_{10}$-phenylalkyl mono- to tri-substituted in the phenyl moiety by $C_1$–$C_4$-alkoxy, more preferably $C_7$–$C_{10}$-phenylalkyl mono- to tri-substituted in the phenyl moiety by $C_1$–$C_2$-alkoxy, such as 4-methoxybenzyl, 4-ethoxybenzyl, and 4-methoxyphenethyl, $C_7$–$C_{20}$-arylalkyl mono- to tri-substituted in the aryl moiety by $C_1$–$C_4$-haloalkyl, preferably $C_7$–$C_{10}$-phenylalkyl mono- to tri-substituted in the phenyl moiety by $C_1$–$C_2$-fluoroalkyl and $C_1$–$C_2$-chloroalkyl, more preferably $C_7$–$C_{10}$-phenylalkyl mono- to tri-substituted in the phenyl moiety by trifluoromethyl and trichloromethyl, such as 4-trifluoromethylbenzyl and 4-trichloromethylbenzyl, $C_7$–$C_{20}$-arylalkyl mono- to tri-substituted in the aryl moiety by $C_1$–$C_4$-haloalkoxy, preferably $C_7$–$C_{10}$-phenylalkyl mono- to tri-substituted in the phenyl moiety by $C_1$–$C_2$-haloalkoxy, more preferably $C_7$–$C_{10}$-phenylalkyl $C_1$–$C_2$-haloalkoxy, more preferably $C_7$–$C_{10}$-phenylalkyl mono- to tri-substituted in the phenyl moiety by trifluoromethoxy and trichloromethoxy, such as 4-trifluoromethoxybenzyl and 4-trichloromethoxybenzyl, $C_7$–$C_{20}$-arylalkyl mono- to tri-substituted by halophenyl, preferably $C_7$–$Cl_2$-phenylalkyl mono- to tri-substituted by fluorophenyl and/or chlorophenyl, such as 4-chlorophenethyl and 4-fluorophenethyl, $C_7$–$C_{20}$-arylalkyl mono- to tri-substituted by halophenoxy, preferably $C_7$–$Cl_2$-phenylalkyl mono- to tri-substituted by fluorophenoxy and/or chlorophenoxy, such as 2-chlorophenoxymethyl and 4-chlorophenoxymethyl, $C_7$–$C_{20}$-arylalkyl mono- to tri-substituted by carboxy, preferably $C_7$–$C_{12}$-phenylalkyl mono- to tri-substituted by carboxy, such as 4-carboxybenzyl, 4-carboxyphenethyl, 2-carboxybenzyl, and 4-carboxyphenylethyl, $C_7$–$C_{20}$-arylalkyl mono- to tri-substituted by $C_2$–$C_8$-alkoxycarbonyl, preferably $C_7$–$Cl_2$-phenylalkyl mono- to tri-substituted by $C_2$–$C_4$-alkoxycarbonyl, such as 4-methoxycarbonylbenzyl, 2-methoxycarbonylbenzyl, 4-ethoxycarbonylbenzyl, and 2-ethoxycarbonylbenzyl, $C_7$–$C_{20}$-arylalkyl mono- to tri-substituted by cyano, preferably $C_7$–$C_{12}$-phenylalkyl mono- to tri-substituted by cyano, such as 2-cyanobenzyl, 4-cyanobenzyl, 2-cyanophenethyl, and 4-cyanophenethyl, phenyl substituted by one, two, or three phenyl groups, such as 2-(phenyl)phenyl, 3-(phenyl)phenyl, 4-(phenyl)phenyl, and 3,4-(diphenyl)phenyl, phenyl substituted by one, two, or three phenoxy groups, such as 4-phenoxyphenyl and 2-phenoxyphenyl, phenyl di- or tri-substituted by halogen and $C_1$–$C_4$-4-fluorophenyl, phenyl di- or tri-substituted by halogen and $C_1$–$C_4$-alkoxy, such as 3-chloro-4-methoxyphenyl, phenyl di- or tri-substituted by halogen and $C_1$–$C_4$-haloalkyl, such as 2-chloro-4-trifluoromethylphenyl, phenyl di- or tri-substituted by halogen and phenoxy, such as 3-chloro-4-phenoxyphenyl, phenyl di- or tri-substituted by $C_1$–$C_4$-alkyl and $C_1$–$C_4$-alkoxy, such as 2-methyl-4-methoxyphenyl, phenyl di- or tri-substituted by $C_1$–$C_4$-alkyl and $C_1$–$C_4$-haloalkyl, such as 3-methyl-4-trichloromethylphenyl, phenyl di- or tri-substituted by $C_1$–$C_4$-alkyl and phenoxy, such as 2-methyl-4-phenoxyphenyl, phenyl di- or tri-substituted by $C_1$–$C_4$-alkoxy and $C_1$–$C_4$-haloalkyl, such as 3-trifluoromethyl-4-methoxyphenyl, phenyl di- or tri-substituted by $C_1$–$C_4$-alkoxy and phenoxy, such as 3-methoxy-4-phenoxyphenyl, phenyl di- or tri-substituted by $C_1$–$C_4$-haloalkyl and phenoxy, such as 3-trifluoromethyl-4-phenoxyphenyl, phenyl trisubstituted by halogen, $C_1$–$C_4$-alkyl, and $C_1$–$C_4$-alkoxy, such as 2-chloro-3-t-butyl-4-methoxyphenyl, phenyl trisubstituted by halogen, $C_1$–$C_4$-alkyl, and $C_1$–$C_4$-haloalkyl, such as 2-methyl-3-chloro-4-trifluoromethylphenyl, phenyl trisubstituted by halogen, $C_1$–$C_4$-alkyl, and phenoxy, such as 4-chloro-2-ethyl-3-phenoxyphenyl, phenoxy, such as 4-chloro-2-ethyl-3-phenoxyphenyl, phenyl trisubstituted by halogen, $C_1$–$C_4$-alkoxy, and $C_1$–$C_4$-haloalkyl, such as 3-chloro-4-methoxy-3-trifluoromethyl, phenyl trisubstituted by halogen, $C_1$–$C_4$-alkoxy, and phenoxy, such as 2-fluoro-4-ethoxy-3-phenoxyphenyl, phenyl trisubstituted by halogen, $C_1$–$C_4$-haloalkyl, and phenoxy, such as 4-fluoro-3-trifluoromethyl-2-phenoxyphenyl, phenyl trisubstituted by $C_1$–$C_4$-alkyl, $C_1$–$C_4$-alkoxy, and $C_1$–$C_4$-haloalkyl, such as 4-methyl-3-methoxy-2-trichloromethylphenyl, phenyl trisubstituted by $C_1$–$C_4$-alkyl, $C_1$–$C_4$-alkoxy, and phenoxy, such as 4-methyl-3-ethoxy-2-phenoxyphenyl, phenyl trisubstituted by $C_1$–$C_4$-alkyl, $C_1$–$C_4$-haloalkyl, and phenoxy, such as 2-methyl-4-trifluoromethyl-3-phenoxyphenyl, phenyl trisubstituted by $C_1$–$C_4$-alkoxy, $C_1$–$C_4$-haloalkyl, and phenoxy, such as 4-methoxy-2-trichloromethyl-3-phenoxyphenyl, or $R^7$ and $R^8$ or $R^7$ and $R^9$ or $R^7$ and $R^{10}$ or $R^9$ and $R^{10}$ or $R^{10}$ and $R^{11}$ together form $(CH_2)_n$, such as $CH_2$, $(CH_2)_2$, $(CH_2)_3$, $(CH_2)_4$, $(CH_2)_5$, and $(CH_2)_6$, preferably $(CH_2)_3$, $(CH_2)_4$, $(CH_2)_5$, and $(CH_2)_6$, more preferably $(CH_2)_3$ and $(CH_2)_4$, n an integer from 1 to 6, preferably from 3 to 6, more preferably 3 or 4, $R^{12}$—hydrogen, $C_1$–$C_8$-alkyl, preferably $C_1$–$C_4$-alkyl, such as methyl, benzyl, provided that $R^{10}$ is not hydrogen, methyl, ethyl, propyl, or cyclohexyl when $R^7$, $R^8$, $R^9$, or $R^{11}$ is hydrogen, that $R^7$ is not methyl when $R^8$ is methyl or phenyl and $R^9$, $R^{10}$, or $R^{11}$ is hydrogen, that $R^7$ is not methyl when $R^8$, $R^9$, $R^{10}$, or $R^{11}$ is hydrogen and $R^{12}$ is ethyl, that $R^7$ is not phenyl or hexyl when $R^8$, $R^9$, $R^{10}$, or $R^{11}$ is hydrogen, that $R^9$ is not methyl when $R^7$, $R^8$, $R^{10}$, or $R^{11}$ is hydrogen, that $R^{10}$ and $R^{11}$ are not methyl when $R^7$, $R^8$, or $R^9$ is hydrogen, and that $R^7$ and $R^{10}$ do not together form an unsubstituted cycloalkyl when $R^8$, $R^9$, or $R^{11}$ is hydrogen.

The compounds of the invention I and IV serve as intermediates for the synthesis of, inter alia, perfumes, plant protectants, and polymers.

EXAMPLES

Example 1

Electrosynthesis of 2,3-epoxy-1-methoxyoctane

Oct-1-en-3-ol is oxidized in the electrolytic cell described below under the conditions stated:

Apparatus: undivided cell equipped with 9 bipolar electrodes

Anode: graphite

Electrolyte: 62.5 g (488 mmoles) of oct-1-en-3-ol, 15 g of NaBr, 12.5 g of $H_2O$, 535 g of methanol Cathode: graphite Current density: 6.3 A/dm$^2$ Electrolysis temperature: 60° C.

The electrolysis is effected at a capacity rating of 4.75 F per mole of oct-1-en-3-ol. During electrolysis, the electrolyte is pumped through the cell at a rate of 20 l/h. On completion of the electrolysis, the methanol is distilled off under atmospheric pressure and the precipitated conductive salt is isolated by filtration. The product is purified by distillation in vacuo and there are obtained 5.4 g (42 mmoles) of unconverted oct-1-en-3-ol and 28.6 g (37%) of 2,3-epoxy-1-methoxyoctane as a mixture of cis and trans isomers, b.p. 92° C./22 mbar.

Example 2

Electrosynthesis of 1,2-epoxy-3-methoxy-3-methylbutane

4-Methyl-2-buten-1-ol is electrochemically oxidized under the conditions described in Example 1.

Electrolyte: 62.5 g (727 mmoles) of 4-methyl-2-buten-1-ol, 15 g of NaBr and 547.5 g of methanol.

The electrolysis is carried out at a rating of 4.4 F per mole of prenol. During electrolysis, the electrolyte is pumped through the cell at a rate of 20 l/h. The effluent is worked up as described in Example 1. Purification by distillation at atmospheric pressure gives 2.5 g (29 mmoles) of unconverted educt and 46.9 g (56%) of 1,2-epoxy-3-methoxy-3-methylbutane, b.p. 115° to 120° C./1013 mbar.

Example 3

Electrosynthesis of 1,2-epoxy-3-methoxybutane

Crotyl alcohol is electrochemically oxidized under the conditions described in Example 1.

Electrolyte: 62.5 g (868 mmoles) of crotyl alcohol, 15 g of NaBr, and 547.5 g of methanol.

The electrolysis rating is 5 F per mole of crotyl alcohol. During electrolysis, the electrolyte is pumped through the cell at a rate of 20 l/h. The effluent is worked up as described in Example 1. Purification by distillation at atmospheric pressure gives 8.5 g (118 mmoles) of unconverted crotyl alcohol and 1,2-epoxy-3-methoxybutane in a yield of 58% (51.2 g), b.p. 105–110° C./1013 mbar.

Example 4

Electrosynthesis of 1,2-epoxy-3-methoxy-3-phenylpropane

3-Phenyl-2-propen-1-ol is oxidized under the conditions described in Example 1 in an undivided cell equipped with 11 bipolar electrodes.

Electrolyte: 300 g (2.239 moles) of 3-phenyl-2-propen-1-ol, 60 g of NaBr, and 2,640 g of methanol Current density: 3.4 A/dm$^2$ Electrolysis is carried out at a rating of 5 F per mole of cinnamyl alcohol. During electrolysis, the electrolyte is pumped through the cell at a rate of 200 l/h. The effluent is worked up as described in Example 1. Purification by distillation in vacuo retrieves 17.5 g (58 mmoles) of educt and gives 187.5 g (51%) of 1,2-epoxy-3-methoxy-3-phenylpropane, b.p. 86° C./3 mbar.

Example 5

Electrosynthesis of 2,3-epoxy-1-methoxynonane

Non-1-en-3-ol is oxidized under the conditions described in Example 1 in an undivided cell equipped with 11 bipolar electrodes.

Electrolyte: 300 g (2.113 moles) of non-1-en-3-ol, 60 g of NaBr, 60 g of water, and 2,580 g of methanol Current density: 3.4 A/dm$^2$ The electrolysis is carried out at a rating of 6.75 F per mole of non-1-en-3-ol. During electrolysis, the electrolyte is pumped through the cell at a rate of 200 l/h. The effluent is worked up and purified by distillation in vacuo to retrieve 15.9 g (112 mmoles) of non-1-en-3-ol and yield 178.6 g (49%) of 2,3-epoxy-1-methoxynonane, b.p. 85–88° C./8 mbar.

Example 6

Electrosynthesis of 4,5-epoxy-6-methoxydecane

Dec-5-en-4-ol is electrochemically oxidized under the conditions described in Example 1.

Electrolyte: 62.5 g (401 mmoles) of dec-5-en-4-ol, 15 g of NaBr, 12.5 g of water, and 535 g of methanol Electrolysis is carried out at a rating of 4 F per mole of dec-5-en-4-ol. During electrolysis, the electrolyte is pumped through the cell at a rate of 20 l/h. The effluent is worked up and purified by distillation to recover 1.4 g (22 mmoles) of dec-5-en-4-ol and yield 21.0 g (28%) of 4,5-epoxy-6-methoxydecane, b.p. 50–52° C./1 mbar.

Example 7

Electrosynthesis of 1,2-epoxy-3-methoxy-3-phenylcyclohexane

3-Phenylcyclohex-2-en-1-ol is electrochemically oxidized under the conditions described in Example 1.

Electrolyte: 40 g (230 mmoles) of 3-phenylcyclohex-2-en-1-ol, 15 g of NaBr, 12.5 g of water, and 535 g of methanol.

Electrolysis is carried out at a rating of 5 F per mole of 3-phenylcyclohex-2-en-1-ol. During electrolysis, the electrolyte is pumped through the cell at a rate of 20 l/h. The effluent is worked up and purified by distillation to give 5.4 g (31 mmoles) of 3-phenylcyclohex-2-en-1-ol and 11.8 g (25%) of 1,2-epoxy-3-methoxy-3-phenylcyclohexane, b.p. 120–125° C./2 mbar.

Example 8

Electrosynthesis of 1-cyclohexyl-1,2-epoxy-3-methoxypropane

1-Cylohexylprop-2-en-1-ol is electrochemically oxidized under the conditions described in Example 1.

Electrolyte: 187.5 g (1.339 moles) of 1-cyclohexylprop-2-en-1-ol, 45 g of NaBr, 37.5 g of water, and 1,605 g of methanol The electrolysis is carried out at a rating of 4.4 F per mole of 1-cyclohexylprop-2-en-1-ol. During electrolysis, the electrolyte is pumped through the cell at a rate of 20 l/h. Following the usual work-up procedure there are obtained 11.4 g (61 mmoles) of unconverted educt and 94.9 g (42%) of 1-cyclohexyl-1,2-epoxy-3-methoxypropane, b.p. 75° C./5 mbar.

Example 9

Electrosynthesis of 2,3-epoxy-4-methoxy-1-phenylbutane

3-Hydroxy-4-phenylbut-1-ene is electrochemically oxidized under the conditions described in Example 1.

Electrolyte: 31.5 g (213 mmoles) of 3-hydroxy-4-phenylbut-1-ene, 8 g of NaBr, 6 g of $H_2O$, and 355 g of methanol The electrolysis is carried out at a rating of 9 F per mole of 3-hydroxy-4-phenylbut-1-ene. During electrolysis, the electrolyte is pumped through the cell at a rate of 13 l/h. The effluent is worked up and distilled to give 3.7 g of unconverted educt and 10.7 g (28%) of 2,3-epoxy-4-methoxy-1-phenylbutane, b.p. 58–63° C./5 mbar.

Example 10

Synthesis of 1,2-epoxy-3-methoxy-3-methylbutane by oxidation of 4-methyl-2-buten-1-ol with bromine 25.8 g (300 mmoles) of 4-methyl-2-buten-1-ol, 10 g of a 30% w/w sodium methylate solution, and 240 g of methanol are placed in a vessel and stirred at room temperature (20–21° C.) while 24 g (150 mmoles) of bromine and 44 g of 30% w/w sodium methylate solution are concurrently added dropwise, in two streams, over a period of 2 hours. On completion of the reaction, water is added to the reaction mixture, which is then extracted with methyl-t-butyl ether. The extract is dried and subjected to fractional distillation to give 15.7 g (183 mmoles) of unconverted 4-methyl-2-buten-1-ol and 5.4 g (47 mmoles) of 1,2-epoxy-3-methoxymethylbutane, b.p. 115–120° C./1013 mbar.

We claim:

1. A process for the preparation of an epoxide of formula I

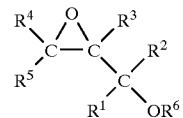

(I)

in which $R^1, R^2, R^3, R^4, R^5$ are selected from the group consisting of hydrogen;

$C_1$–$C_{20}$-alkyl;

$C_3$–$C_{12}$-cycloalkyl;

$C_4$–$C_{20}$-cycloalkylalkyl;

$C_1$–$C_{20}$-hydroxyalkyl;

a heterocyclic ring;

aryl;

$C_7$–$C_{20}$-arylalkyl, which is either unsubstituted or substituted by a member selected from the group consisting of $C_1$–$C_8$-alkyl, $C_1$–$C_8$-alkoxy, halogen, $C_1$–$C_4$-haloalkyl, $C_1$–$C_4$-haloalkoxy, phenyl, phenoxy, halophenyl, halophenoxy, carboxy, $C_2$–$C_8$-alkoxycarbonyl and cyano; or either of $R^1$ and $R^2$, $R^1$ and $R^3$, $R^1$ and $R^4$, $R^3$ and $R^4$, or $R^4$ and $R^5$ together form a $(CH_2)_n$ group in which n is an integer of from 1 to 10; wherein the $(CH_2)_n$ group is unsubstituted or substituted by a member selected from the group consisting of $C_1$–$C_5$-alkyl, $C_1$–$C_8$-alkoxy and halogen, or a combination thereof; and $R^6$ is hydrogen $C_1$–$C_8$-alkyl or benzyl:

which process comprises a) electrochemically oxidizing an allyl alcohol of formula II

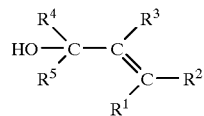

(II)

in the presence of both an auxiliary electrolyte and compound of formula III $R^7$—OH　　　　　III where $R^7$ is $C_1$–$C_8$-alkyl or benzyl; or b) oxidizing an allyl alcohol of formula 11, as defined above, with halogen in the presence of a compound of formula III, as defined above, at a pH of from 7.5 to 14.

2. A process for the, preparation of an epoxide of the formula I as defined in claim 1, wherein the reactions are carried out at a temperature of from 0° to 100° C.

3. A process as defined in claim 1, wherein the electrolyte used for the electrochemical oxidation is composed of from 1 to 49% w/w of an allyl alcohol of formula II, from 50 to 98.9% w/w of an alcohol of formula III, and from 0.1 to 5% w/w of an auxiliary electrolyte.

4. A process as defined in claim 1, wherein the electrochemical oxidation is carried out using graphite electrodes.

5. A process as defined in claim 1, wherein the electrochemical oxidation is carried out at current densities ranging from 0.5 to 25 A/dm$^2$.

6. A process as defined in claim 1, wherein the auxiliary electrolyte used comprises an iodide or a bromide.

7. A process according to claim 1 wherein at least one of the substituents $R^1$, $R^2$, $R^3$, $R^4$, and $R^5$, is not hydrogen.

* * * * *

UNITED STATES PATENT AND TRADEMARK OFFICE
CERTIFICATE OF CORRECTION

PATENT NO.: 5,916,430

DATED: June 29, 1999

INVENTOR(S): Dieter HERMELING

It is certified that error appears in the above-identified patent and that said Letters Patent is hereby corrected as shown below:

Col. 14, claim 1, line 33, "$C_1$-$C_5$-alkyl" should be --$C_1$-$C_8$-alkyl--.

Col. 14, claim 2, line 59, delete the comma "," which appears after the word "the".

Signed and Sealed this

Ninth Day of November, 1999

Attest:

Q. TODD DICKINSON

*Attesting Officer*    *Acting Commissioner of Patents and Trademarks*